United States Patent [19]

Carroll et al.

[11] Patent Number: 4,776,857

[45] Date of Patent: Oct. 11, 1988

[54] USE OF HYDROXYLATED INDOLES AS DYE PRECURSORS

[75] Inventors: James Carroll, Cambridge, Mass.; Cynthia D. Millis, Vancouver, Canada; Walter C. Herlihy, Beverly, Mass.

[73] Assignee: Repligen Corporation, Cambridge, Mass.

[21] Appl. No.: 933,649

[22] Filed: Nov. 21, 1986

[51] Int. Cl.$^4$ .................. A61K 7/13; A61K 7/42; A61K 7/44

[52] U.S. Cl. ............................... 8/423; 8/405; 8/406; 8/409; 8/429; 424/59; 424/63

[58] Field of Search ................ 8/405, 406, 409, 423, 8/429; 424/59, 63

[56] References Cited

U.S. PATENT DOCUMENTS

| | | | |
|---|---|---|---|
| 2,934,396 | 4/1960 | Charle et al. | 8/423 |
| 3,993,436 | 11/1976 | Fujinuma | 8/423 |
| 4,013,404 | 3/1977 | Parent et al. | 8/423 |
| 4,021,538 | 5/1977 | Yu et al. | 8/405 |
| 4,208,183 | 6/1980 | Grollier et al. | 8/409 |
| 4,390,341 | 6/1983 | Jacobs | 8/405 |
| 4,515,773 | 5/1985 | Herlihy | 424/59 |
| 4,609,544 | 9/1986 | Herlihy | 424/63 |

FOREIGN PATENT DOCUMENTS

| | | |
|---|---|---|
| 161073 | 11/1985 | European Pat. Off. . |
| 3031709 | 4/1982 | Fed. Rep. of Germany .......... 8/409 |

OTHER PUBLICATIONS

Crebelli, R. et al., "Mutagenicity of Commercial P—Phenylenediamine and of an Oxidation Mixture of P—Phenylenediamine and Resorcinol in *Salmonella typhimurium* TA98" Fd. Cosmet. Toxicol. 19:79–84 (1981).

*Primary Examiner*—Paul Lieberman
*Assistant Examiner*—Linda D. Skaling
*Attorney, Agent, or Firm*—Roman Saliwanchik; David R. Saliwanchik

[57] ABSTRACT

The invention concerns a new system to dye hair and/or skin. The system comprises the use of a hydroxyindole dye precursor and sodium periodate. Advantageously, this dye system allows the dye to penetrate inside the hair fiber without coating the hair shaft and, thus, give a more pleasing and stable dye result.

27 Claims, No Drawings

USE OF HYDROXYLATED INDOLES AS DYE PRECURSORS

DESCRIPTION

Background of the Invention

In the past thirty years a variety of chemical systems for dyeing hair have been developed. The most commercially successful of these has utilized phenylenediamine combined with various couplers and modifiers with hydrogen peroxide as the oxidant. Although this system covers gray well it suffers from a number of problems: Phenylenediamine is a known sensitizer; the hair is damaged by repeated exposure to alkaline peroxide; and the color produced may fade over time to an off shade. Furthermore, p-phenylenediamine is oxidized in the presence of resorcinol by hydrogen peroxide to a mutagen that is percutaneously absorbed. (See: Crebelli, R., Conti, L., Carere, A. and Zito, A. [1981] "Mutagenicity of Commercial p-Phenylenediamine and of an Oxidation Mixture of p-Phenylenediamine and Resorcinol in *Salmonella typhimurium* TA98" Fd. Cosmet. Toxicol. 19: 79–84.)

The formation of melanin-like dye has previously been described using dopamine as the dye precursor and sodium iodate or sodium periodate as the oxidant. See European Patent Application No. 85302457.8, published Nov. 13, 1985, No. 0161073. The most important pathway for the formation of melanin in vivo involves oxidation of dopa to dopaquinone which then in turn cyclizes to form leucodopachrome in the case of dopa. Leucodopachrome is then oxidized to dopachrome which rearranges with the loss of carbon dioxide to yield 5,6-dihydroxyindole which subsequently undergoes oxidative polymerization to form melanin.

Related U.S. Pat. No. 4,021,538 concerns a "Method for Producing Pigmentation in Hair or Skin" by use of esters of dopa because of their solubility in both water and lipid solvents. U.S. Pat. No. 4,390,341 concerns a composition for coloring hair or skin which employs, inter alia, acylated dopamine or acylated tyrosine derivatives and omega amino acids. U.S. Pat. No. 2,934,396 concerns a composition for coloring hair and other keratinous material which employs 5,6-dihydroxyindole as the dye precursor. However, U.S. Pat. No. 4,208,183 discloses that commercial exploitation of 5,6-dihydroxyindole-dyestuffs is limited due to the lack of stability during storage of 5,6-dihydroxyindole.

At this time in the hair dyeing art it is clear that a need exists for an effective melanin-like dye composition to color hair to a pleasing black, brown or other color; or for use as a skin tanning composition. Such a dye composition desirably should be non-toxic, do minimal to no damage to the hair and skin, and impart a desired color that is stable to repeated washings and weathering. The novel hair dye composition and dyeing process of the subject invention is a distinct improvement over commercially-available hair dyes and processes for using the same. Further, the compositions and processes of the subject invention are neither disclosed nor suggested by known prior art procedures.

BRIEF SUMMARY OF THE INVENTION

We have made a surprising discovery that monohydroxyindoles, as disclosed herein, formed, advantageously and desirably, melanin-like dyes of varying shades when oxidized with sodium periodate (preferred), and other oxidants. For example, 4-, 5-, 6-, and 7-hydroxyindoles form a black, dark chestnut brown, dark brown, and a red-brown dye, respectively, when oxidized by sodium periodate or by oxygen and UV light at room temperature. Hair dyed with either 4-, 5-, 6-, or 7-hydroxyindole was stable to multiple shampooing. A number of oxidants effected dye formation for topical applications; however, surprisingly, only sodium periodate but not sodium iodate, effected dye formation inside the hair shaft. Skin and other keratinous material may also be dyed or stained by the hydroxyindoles, either alone or in combinations. Other hydroxylated indole analogues, for example, indole-5-hydroxy-3-acetic acid and indole-5-hydroxy-2-carboxylic acid resulted in less color formation. Hydroxyindole precursors also appear to be advantageous over dihydroxyindoles, i.e., 5,6-dihydroxyindole, in that they are more stable during storage. The dye system of the subject invention has proven to be useful in dyeing both human hair and skin. In addition, this malenin-like dye system has a surprising and advantageous property in that the dye causes minimal or no damage to the hair as compared to the damage caused to hair by the p-phenylenediamine-type dyes. The color is stable to washing in that after a large number of washings (e.g., 10), the color is maintained. Thus, this process avoids the red or green overtones which are often observed after repeated washing or perming of hair colored with commercially available phenylenediamine-based dyes.

Another advantageous property of the subject invention may be protection of the hair and skin against damage by ultraviolet light.

DETAILED DESCRIPTION OF THE INVENTION

The unique dyeing combination of the subject invention comprises (1) a hydroxyindole dye precursor and (2) an oxidant, preferably sodium periodate.

The hydroxyindole dye precursors useful in the subject invention can be shown as follows:

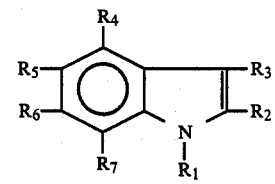

wherein
$R_1$ is H or alkyl (1–4C);
$R_4$, $R_5$, $R_6$, $R_7$ can be the same or different but one must be OH and the others selected from: H, alkyl (1–4C), $NH_2$, COOR' (R' is alkyl 1–4C or H), $CONH_2$, halogen (Cl, Br, I, F), OR" (R" is alkyl 1–4C); $CH_2OH$, $CH_2NH_2$, CONR'R" wherein R' and R" can be the same or different;
$R_2$, $R_3$ can be the same or different and are: H, OH, alkyl (1–4C), $NH_2$, COOR' (R' is alkyl 1–4C or H), $CONH_2$, halogen (Cl, Br, I, F), OR" (R" is alkyl 1–4C); $CH_2OH$, $CH_2NH_2$, CONR'R" wherein R' and R" can be the same or different. The dye precursor can be used alone or in a mixture of dye precursors.

A screening of oxidants was performed with hydroxyindoles to determine if they would promote the formation of a melanin-like dye. Several oxidants promoted the polymerization of hydroxyindoles in solution, namely, oxygen in the presence of UV light, sodium periodate, potassium permanganate, sodium hypochlorite, potassium ferricyanide, potassium dichromate, ammonium persulfate, silver oxide, Fentons reagent, ferric chloride, lead (IV) oxide, and cesium (IV) sulfate. However, surprisingly, sodium periodate was the most efficient oxidant for melanin dye formation inside the hair.

Currently commercially available hair dye products are formulated so that the dye precursors are stored in one bottle and the oxidant is stored in a second bottle. Immediately before use the two are mixed together and subsequently applied to the hair. After an appropriate interval of time the hair is rinsed and washed, leaving the hair dyed. Since only one solution is applied to the hair and the process requires only a rinse at the end, this has been defined as a onestep process.

Sodium periodate cannot be employed as the oxidant in the one-step process since the dye precursors require sufficient time to penetrate into the hair fibers before sodium periodate is introduced into the dye bath.

Two hair dye processes have been developed to overcome the dye precursor penetration-time problem. The first process, designated the two-step process, requires applying the dye precursor to the hair, waiting about 3 to about 30 min, rinsing the hair, applying the periodate solution to the hair, waiting about 3 to about 30 min, and then rinsing the hair. In the two-step process a surfactant such as 1% sodium dodecyl sulfate (SDS) may be included in the formulations.

The second process, designated the one and one-half step process, eliminates the intermediate rinse between the application of the dye precursor mixture and the application of the sodium periodate mixture to the hair. For best results a surfactant such as about 0.1–10% SDS should be included in the formulation when the one and one-half step process is utilized, to prevent unwanted surface coating of the hair fibers with dye material.

The one and one-half step process may be converted to a one-step process by utilizing chemical as well as physical methods of delaying periodate introduction into the dye bath, e.g., utilizing slightly soluble salts of periodate, utilizing liposome technologies, or utilizing microencapsulation technologies.

Generally, the dyeing system of the subject invention can be applied to hair or skin in the following manner.

Hair (Two-step process)

The hair is contacted with an aqueous solution (which can include 0.1–10% of a surfactant such as SDS or CYCLOPOL SBFA 30 (disodium laureth sulfosuccinate) [Cyclo Chemical Co., Miami, FL]) of about 0.1 to about 10% of a hydroxyindole dye precursor (for convenience the bath ratio [liquid: hair] can be 0.5:1 to 5:1) at room temperature for about 3 to about 30 min. The hair is rinsed with water, patted dry, and then contacted with a solution of about 3 to about 15% of sodium periodate (for convenience the bath ratio [liquid:hair] can be 0.5:1 to 5:1), which can include 0.1–10% of a surfactant such as SDS or CYCLOPOL SBFA 30 at about 20° to about 30° C. for about 5 to about 30 min. Dyeing is terminated by rinsing the hair with water, followed, if desired, by one or two one-minute washings with a commercially-available mild shampoo. The hair then can be combed out and blown dry, if desired.

Hair (One and one-half step process)

The hair is contacted with an aqueous solution (which can include 0.1–10% of a surfactant such as SDS or CYCLOPOL SBFA 30) of about 0.1 to about 10% of a hydroxyindole dye precursor (for convenience the bath ratio [liquid:hair] can be 0.5:1 to 5:1) at room temperature for about 3 to about 30 min. The hair is subsequently contacted with a solution of about 3 to about 15% of sodium periodate (for convenience the bath ratio [liquid:hair] can be 0.5:1 to 5:1), which can include 0.1–10% of a surfactant such as SDS or CYCLOPOL SBFA 30 at about 20° to about 30° C. for about 5 to about 30 min. Dyeing is terminated by rinsing the hair with water, followed, if desired, by one or two one-minute washings with a commercially-available mild shampoo. The hair then can be combed out and blown dry, if desired.

Skin

The human skin can be dyed a pleasing tan color by use of essentially the same conditions as disclosed above for dyeing hair except that there is no intermediate rinse and a number of oxidants other than sodium periodate can be employed.

The skin is contacted with an aqueous solution of about 0.1 to about 10% of a hydroxyindole dye precursor at room temperature for about 3 to about 30 min. The skin is subsequently contacted with a solution of an appropriate oxidant, for example, 5 to about 15% of sodium periodate in water, for about 5 to about 30 min. Dyeing is terminated by rinsing the skin with water. The skin is dyed a stable shade. Both 5-hydroxyindole and 6-hydroxyindole dye precursors will stain the skin a natural tan color if used alone. A variety of shades can be obtained by utilizing other hydroxyindoles or mixtures of hydroxyindoles at a variety of concentrations.

In another procedure the skin is contacted with a formulation containing about 0.1 to about 10% of a hydroxyindole dye precursor, a cosmetic carrier such as SYLOID 63 (Davison Chemical Co., Baltimore MD) and a solvent such as water or ethanol. Upon subsequent exposure to UV radiation of skin which has been contacted with the topical dye material, the skin is stained a pleasing tan shade, especially if 5- or 6-hydroxyindole is utilized.

In a third procedure the skin is contacted with a solution or suspension of preformed hydroxyindole dye products in an appropriate carrier such as water or ethanol. After the carrier has evaporated, the skin is stained a pleasant tan color, especially if 5-hydroxyindole preformed dye product is utilized.

Formation of Dyes Utilizing Hydroxyindoles

A variety of indole derivatives were tested on hair. The ability of several indole derivatives to form a dye inside hair are shown in Table 1. It can be seen that the presence of a hydroxyl group on the aromatic ring is required in order to form a dye. 4-, 5-, 6-, and 7-Hydroxyindoles were found to form a black, dark brown, dark brown, and red-brown dye, respectively. The intensity or shades of color desired will dictate the choice of dye precursor. The addition of an acetate or carboxylate group to the 2- or 3-position of the indole ring reduces the color of the dye formed as seen with indole-5-hydroxy-3-acetic acid and indole-5-hydroxy-2-carboxylic acid (Table 1).

At 25° C. 5-hydroxyindole (2%), 4-hydroxyindole (1%), 6-hydroxyindole (2%) and 7-hydroxyindole (2%) were found to form a dark brown, black, dark brown, and red-brown dye, respectively, inside hair in the dye process when allowed to penetrate hair for 3–15 min and subsequently oxidized with sodium periodate. The formation of melanin-like dye inside the hair (as assessed by light and electron microscopy) can therefore by accomplished utilizing 4-, 5-, 6-, or 7-hydroxyindoles at low concentration employing a room temperature process of a total of about 20 min. Increasing the temperature to 34° C. shortened the total dye time required but did not significantly enhance color formation. Results on the ability of hydroxyindoles to stain skin were similar to those with hair.

A permanent coloring system for hair should produce a dye which is resistant to multiple shampooing. A staining or tanning system for skin should produce a stain which is resistant to several washings. The stability of melanin-like dye in hair formed by either 4-, 5-, 6-, or 7-hydroxyindole to shampooing was investigated. Tresses were exposed to either 4-hydroxyindole (1%), 5-hydroxyindole (2%), 6-hydroxyindole (2%) or 7-hydroxyindole (2%) for 15 min followed by a rinse and then by a 15-min oxidation by sodium periodate (15%). Tresses which were washed either one time (wash/rinse/wash/rinse) or ten times were indistinguishable from each other. Thus, the dye formed by either 4-, 5-, 6-, or 7-hydroxyindole in the hair is stable to shampooing.

Upon light microscopic examination of cross sections of hair fibers treated with hydroxyindoles and the oxidants that showed effectiveness is converting the hydroxyindoles to melanin-like dyes in solution, only the hair fibers treated with periodate or its salts visually contained dye material within the fiber with little or no damage to the hair cuticle, and little to no coating of the dye on the hair surface. Potassium permanganate effected some dye formation within the hair fibers examined; however, the cuticles of the hair fibers treated were severely damaged during the dyeing process.

Mixtures of 4-hydroxyindole (0.1-10%) and 5-hydroxyindole (0.1-10%), 6-hydroxyindole (0.1-10%), or 7-hydroxyindole (0.1-10%) will give a color range from black to light auburn. 5-Hydroxyindole (0.1-10%) was found to produce progressively darker browns and, eventually, black through the addition of 3-methylcatechol (0.1-10%), 3-methoxycatechol (0.1-10%), or 3,6-dimethylcatechol (0.1-10%) followed by oxidation by sodium periodate (15%). 4-Hydroxyindole (1%) was found to produce progressively lighter colors with increasing red highlights through the addition of dopamine (2-5%) when penetration of precursors was done at high pH (9.2). Therefore a range of colors from light brown to black can be obtained through combinations of 4-hydroxyindole, 5-hydroxyindole, 6-hydroxyindole, and 7-hydroxyindole with each other or various other dye precursors. Similar results were obtained in staining skin in that a range of shades from light to dark brown can be obtained through combinations of hydroxyindoles with various other dye precursors.

If desired, a thickening agent can be incorporated into the dyeing combinations to minimize dripping from the hair or skin. Suitable thickeners include water-soluble resins and gums, for example carrageenan, guar gum, locust bean gum, and the like; also polymers, such as Carbopol 934 (BF Goodrich Chemical Group, Cleveland, OH) polyvinyl alcohol, and the like; or inorganic materials, for example, Veegum (Vanderbilt Company, Norwalk, CN), nonoxynol-4, nonoxynol-9 (Heterene Chemical Co., Paterson, NJ) or combinations of nonoxynols, and the like. A particularly useful thickening agent is polyethylene glycol-150 distearate (PEG-150 distearate) (Heterene). For example, a 10% solution of PEG-150 distearate is compatible with the dyeing reaction and gives a commercially useful thickened product. Thickening agents can be used in a variety of combinations. The thickener can be present at about 0.1 to about 25% by weight, relative to the total weight of the dye composition.

The dyeing time generally can be shortened by dyeing the hair at temperatures above room temperature. For example, more rapid dyeing can be realized at 35° C. than at 20° C. Higher temperatures can be achieved by a variety of methods, including covering the head with a plastic cap during the dyeing reaction; warming of the dye precursor and oxidant solutions before application, either with an external device or with an exothermic reaction initiated by mixing of, for example, the precursor and oxidant solution; with an infrared lamp; or by other means well known in the hair dyeing art.

Anionic, cationic, non-ionic or amphoteric water-soluble surface-active agents also can be included in the dye composition. Surface-active agents such as TEA lauryl sulfate, CYCLOPOL SBFA 30, SIPONIC L-4 (laureth 4) and SIPONIC L-25 (laureth 23) (both supplied by Alcolac, Baltimore, MD), sodium lauryl sulfate, phosphate esters, sodium lauryl ether sulfo succinate, and SDS are examples of such agents known to the art which can be included in the formulation. The surface-active agents are preferably present in the dye composition in a proportion of about 0.1 to about 15% by weight.

Advantageously, a stabilizer can be added to the hydroxyindole composition. A suitable stabilizer is the reducing agent sodium metabilsulfite at a concentration of 1 to about 5 mM. Other reducing agents such as sodium sulfite, ascorbic acid, and the like, can be used.

The subject dye composition can be used in various forms, for example, liquid, cream, gel or an aerosol, or in any other form that is suitable for dyeing hair and human skin.

Following are examples that illustrate products of the invention and procedures. These examples should not be construed as limiting. All percentages are by weight ad all solvent mixture proportions are by volume unless otherwise noted.

EXAMPLE 1

Dyeing Gray Hair to Brown

Gray hair is contacted with an aqueous solution (which may contain a surfactant such as 0.1-10% SDS or CYCLOPOL SBFA 30 and/or a thickening agent such as 5 to 10% PEG-150 distearate) containing 1 to 10% 5-hydroxyindole plus a reducing agent (0.1% ascorbic acid) to prevent premature oxidation of dye precursor (pH 3 to 9) for about 3 to about 15 min at about 20° C. The hair may or may not be rinsed for 30 sec. The hair is then contacted with a solution of about 3 to about 15% sodium periodate (pH 2.5 to 5.5, which may contain a surfactant such as 0.1 to 10% SDS or CYCLOPOL SBFA 30 and/or a thickening agent such as 5 to 10% PEG-150 distearate) and the treatment allowed to proceed for about 10 to about 30 min, after which the hair is rinsed. The hair now has a pleasing and stable brown color with red hairlights.

EXAMPLE 2

Dyeing Gray Hair to Red or Red-Brown

Gray hair is contacted with an aqueous solution (which may contain a surfactant such as 0.1-10% SDS or CYCLOPOL SBFA 30 and/or a thickening agent such as 5 to 10% PEG-150 distearate) containing about 1 to 5% 7-hydroxyindole plus 0.1% ascorbic acid (pH 3 to 9) for about 3 to about 15 min at about 20° C. The hair may or may not be rinsed for 30 sec. The hair is then contacted with a solution of about 3 to about 15% sodium periodate (pH 2.5 to 5.5, which may contain a surfactant such as 0.1 to 10% SDS or CYCLOPOL SBFA 30 and/or a thickening agent such as 5 to 10% PEG-150 distearate) and the treatment allowed to proceed for about 10 to about 30 min, after which the hair is rinsed. The hair now has a pleasing and stable red to red-brown color.

EXAMPLE 3

Dyeing Gray Hair to Red-Brown

Gray hair is contacted with an aqueous solution (which may contain a surfactant such as 0.1–10% SDS or CYCLOPOL SBFA 30 and/or a thickening agent such as 5 to 10% PEG-150 distearate) containing about 1% to about 2% 5-hydroxyindole plus about 0.1% to about 1% 7-hydroxyindole plus 0.1% ascorbic acid (pH 3 to 9) for about 3 to about 15 min at about 20° C. The hair may or may not be rinsed for 30 sec. The hair is then contacted with a solution of about 3 to about 15% sodium periodate (pH 2.5 to 5.5, which may contain a surfactant such as 0.1 to 10% SDS or CYCLOPOL SBFA 30 and/or a thickening agent such as 5 to 10% PEG-150 distearate) and the treatment allowed to proceed for about 10 to about 30 min, after which the hair is rinsed. The hair now has a pleasing and stable red-brown color.

EXAMPLE 4

Dyeing Gray Hair to Black

Gray hair is contacted with an aqueous solution (which may contain a surfactant such as 0.1–10% SDS or CYCLOPOL SBFA 30 and/or a thickening agent such as 5 to 10% PEG-150 distearate) of about 0.5% to about 3% 4hydroxyindole plus 0.1% ascorbic acid (final pH 3 to 9) for about 3 to about 15 min at about 20° C. The hair may or may not be rinsed for 30 sec. The hair is then contacted with a solution of about 3 to about 15% sodium periodate (pH 2.5 to 5.5, which may contain a surfactant such as 0.1 to 10% SDS or CYCLOPOL SBFA 30 and/or a thickening agent such as 5 to 10% PEG-150 distearate) and the treatment allowed to proceed for about 10 to about 20 min, after which the hair is rinsed. The hair now has a pleasing and stable black color.

EXAMPLE 5

Dyeing Gray Hair to Black

Gray hair is contacted with an aqueous solution (which may contain a surfactant such as 0.1 to 10% SDS or CYCLOPOL SBFA 30 and/or a thickening agent such as 5 to 10% PEG-150 distearate) containing about 1% to about 3% 5-hydroxyindole plus about 1 to about 3% 3-methylcatechol plus about 0.1% ascorbic acid (final pH 3-9) for about 3 to about 15 min at 20° C. The hair may or may not be rinsed for 30 sec. The hair is then contacted with a solution of about 3 to about 15% sodium periodate (pH 2.5 to 5.5, which may contain a surfactant such as 0.1 to 10% SDS or CYCLOPOL SBFA 30 and/or a thickening agent such as 5 to 10% PEG-150 distearate) and the treatment allowed to proceed for about 10 to about 20 min, after which the hair is rinsed. The hair now has a pleasing and stable black color.

EXAMPLE 6

Dyeing Gray Hair to Brown

Gray hair is contacted with an aqueous solution (which may contain a surfactant such as 0.1–10% SDS or CYCLOPOL SBFA 30 and/or a thickening agent such as 5 to 10% PEG-150 distearate) containing about 0.1 to about 2% 4-hydroxyindole plus about 2 to about 3% dopamine plus 0.1% ascorbic acid (final pH 7–10) for about 3 to about 15 min at about 20° C. The hair may or may not be rinsed for 30 sec. The hair is then contacted with a solution of about 3 to about 15% sodium periodate (pH 2.5 to 5.5, which may contain a surfactant such as 0.1 to 10% SDS or CYCLOPOL SBFA 30 and/or a thickening agent such as 5 to 10% PEG-150 distearate) and the treatment allowed to proceed for about 10 to about 20 min, after which the hair is rinsed. The hair now has a pleasing and stable brown color.

EXAMPLE 7

Dyeing Gray Hair to Black

Gray hair is contacted with an aqueous solution (which may contain a surfactant such as 0.1 to 10% SDS or CYCLOPOL SBFA 30 and/or a thickening agent such as 5 to 10% PEG-150 distearate) containing about 1% to about 3% 5-hydroxyindole plus about 1 to about 3% 3-methoxycatechol plus about 0.1% ascorbic acid (final pH 3 to 9) for about 3 to about 15 min at 35° C. The hair may or may not be rinsed for 30 sec. The hair is then contacted with a solution of about 3 to about 15% sodium periodate (pH 2.5 to 5.5, which may contain a surfactant such as 0.1 to 10% SDS or CYCLOPOL SBFA 30 and/or a thickening agent such as 5 to 10% PEG-150 distearate) and the treatment allowed to proceed for about 10 to about 20 min at 35° C., after which the hair is rinsed. The hair now has a pleasing and stable black color.

EXAMPLE 8

Dyeing Gray Hair to Dark Brown

Gray hair is contacted with an aqueous solution (which may contain a surfactant such as 0.1 to 10% SDS or CYCLOPOL SBFA 30 and/or a thickening agent such as 5 to 10% PEG-150 distearate) containing about 1 to 10% 6-hydroxyindole plus 0.1% ascorbic acid (final pH 3 to 9) for about 3 to about 15 min at about 25° C. The hair may or may not be rinsed for 30 sec. The hair is then contacted with a solution of about 3 to about 15% sodium periodate (pH 2.5 to 5.5, which may contain a surfactant such as 0.1 to 10% SDS or CYCLOPOL SBFA 30 and/or a thickening agent such as 5 to 10% PEG-150 distearate) and the treatment allowed to proceed for about 10 to about 20 min. The hair now has a pleasing and stable dark brown color.

EXAMPLE 9

Dyeing Gray Hair to Brown

Gray hair is contacted with an aqueous solution (which may contain a surfactant such as 0.1 to 10% SDS or CYCLOPOL SBFA 30 and/or a thickening agent such as 5 to 10% PEG-150 distearate) containing about 0.1% to about 2% 4-hydroxyindole plus about 1 to about 2% 7-hydroxyindole plus 0.1% ascorbic acid (final pH 3–9) for about 3 to about 15 min at about 20°

C. The hair may or may not be rinsed for 30 sec. The hair is then contacted with a solution of about 3 to about 15% sodium periodate (pH 2.5 to 5.5, which may contain a surfactant such as 0.1 to 10% SDS or CYCLOPOL SBFA 30 and/or a thickening agent such as 5 to 10% PEG-150 distearate) and the treatment allowed to proceed for about 10 to about 20 min, after which the hair is rinsed. The hair now has a pleasing and stable brown color with red highlights.

EXAMPLE 10

Dyeing Gray Hair to Brown

Gray hair is contacted with an aqueous solution (which may contain a surfactant such as 0.1 to 10% SDS or CYCLOPOL SBFA 30 and/or a thickening agent such as 5 to 10% PEG-150 distearate) containing about 1 to about 2% 5-hydroxyindole plus about 0.1 to about 1% 3-methylcatechol plus 0.1% ascorbic acid (pH 3–9) for about 3 to about 15 min at about 20° C. The hair may or may not be rinsed for 30 sec. The hair is then contacted with a solution of about 3 to about 15% sodium periodate (pH 2.5 to 5.5, which may contain a surfactant such as 0.1 to 10% SDS or CYCLOPOL SBFA 30 and/or a thickening agent such as 5 to 10% PEG-150 distearate) and the treatment allowed to proceed for about 10 to about 20 min, after which the hair is rinsed. The hair now has a pleasing and stable brown color.

EXAMPLE 11

Dyeing Gray Hair to Black

Gray hair is contacted with an aqueous solution (which may contain a surfactant such as 0.1 to 10% SDS or CYCLOPOL SBFA 30 and/or a thickening agent such as 5 to 10% PEG-150 distearate) containing about 1 to about 2% 6-hydroxyindole plus about 0.1 to about 1% 3-methoxycatechol plus 0.1% ascorbic acid (pH 3 to 9) for about 5 to about 15 min at about 25° C. The hair may or may not be rinsed for 30 sec. The hair is then contacted with a solution of about 5 to about 15% sodium periodate (pH 2.5 to 5.5, which may contain a surfactant such as 0.1 to 10% SDS or CYCLOPOL SBFA 30 and/or a thickening agent such as 5 to 10% PEG-150 distearate) and the treatment allowed to proceed for about 10 to about 20 min, after which the hair is rinsed. The hair now has a pleasing and stable brown color.

EXAMPLE 12

Dyeing Skin to Light Brown

A 2% solution of 6-hydroxyindole was applied to a patch of human skin followed by an equal volume of about 15% sodium periodate. After about 15 min, excess dye was rinsed away with water and the skin was dyed a light brown.

EXAMPLE 13

Dyeing Skin to Brown

A 3% solution of 6-hydroxyindole was applied to a patch of human skin followed by an equal volume of about 10% sodium periodate. After about 10–15 min excess dye was rinsed away with water and the skin was dyed a brown color.

EXAMPLE 14

Dyeing Skin to Brown

A 3% solution of 6-hydroxyindole contained within a cosmetic carrier mixture, such as 10% SILOID 63 and $H_2O$, is applied to human skin. The skin coated with the dye mixture is subsequently exposed to UV radiation for 15 to 60 min. The dye carrier is subsequently rinsed from the skin, leaving the skin stained a stable brown color.

EXAMPLE 15

Dyeing Skin to Brown

A preformed hydroxyindole dye product was formed by reacting a 2% solution of 5-hydroxyindole in $H_2O$ with an equal volume of a 10% sodium periodate solution. After 15 min at room temperature the precipitate was collected and dried. A 2% suspension of this preformed dye product in ethanol was applied to human skin. After the carrier had evaporated, the skin was stained a brown color.

The oxidant which can be used in the subject invention is selected from sodium periodate, periodic acid, other water-soluble salts of periodate, and any of the isolated equilibrium species of periodate. Specifically, periodic acid and salts of lithium, sodium, potassium, rubidium, cesium, magnesium, calcium, strontium, bromine, lanthanum, manganese, iron, copper, zinc, and aluminum can be used.

Other equilibrium states of periodate are as follows:

In an aqueous solution (pH=0–7) periodic acid exists as an equilibrium mixture between the free acid ($H_5IO_6$) and its various ions. A shift in equilibrium would be expected on changing the pH, on dilution, or on mixing with an organic solvent $$H_5IO_6 \rightleftharpoons H_4IO_6^- + H^+$$

$$H_4IO_6^- \rightleftharpoons IO_4^- + 2H_2O$$

$$H_4IO_6^- \rightarrow H_3IO_6^{2-} + H^+$$

$$H_3IO_6^{2-} \rightleftharpoons H_2IO_6^{3-} + H^+$$

$$2H_3IO_6^{2-} \rightleftharpoons H_2I_2I_{10}^{4-} + 2H_2O \text{ (pH=10)}$$

Any of these chemical species and many others could be trapped and isolated and when placed into solution would re-equilibrate to the other chemical species.

TABLE 1

| Ability of Indole Derivatives to Form a Dye | |
|---|---|
| I. Numbering of Indole Ring | |

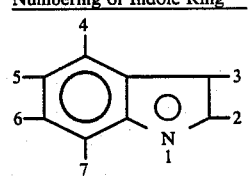

| II. Indole Derivatives Precursor (2% Solution) | Result |
|---|---|
| Indole | — |
| Indole-5-carboxylic acid | Light brown |
| Indole-3-acetic acid | Light brown |
| Indole-3-acetic acid ethyl ester | Light brown |
| 4-Hydroxyindole | Black |
| 5-Hydroxyindole | Dark brown |
| 6-Hydroxyindole | Dark brown |
| 7-Hydroxyindole | Red-brown |

TABLE 1-continued

| Ability of Indole Derivatives to Form a Dye | |
|---|---|
| Indole-5-hydroxy-3-acetic acid | Light brown |
| Indole-5-hydroxy-2-carboxylic acid | Light brown |

We claim:
1. A dye composition for dyeing hair comprising:
(1) a dye precursor consisting of (a) from about 0.1 to about 10% by wt. of a hydroxyindole dye precursor of the formula

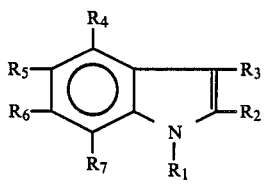

wherein
$R_1$ is H or alkyl (1-4C);
$R_4$, $R_5$, $R_6$, $R_7$ can be the same or different but one must be OH and the others selected from: H, alkyl (1-4C), $NH_2$, COOR' (R' is alkyl 1-4C or H), $CONH_2$, halogen (Cl, Br, I, F), OR" (R" is alkyl 1-4C); $CH_2OH$, $CH_2NH_2$, CONR'R" wherein R' and R" can be the same or different;
$R_2$, $R_3$ can be the same or different and are: H, alkyl, (1-4C), $NH_2$, OH, COOR' (R' is alkyl 1-4C or H), $CONH_2$, halogen, (Cl, Br, I, F), OR" (R" is alkyl 1-4C); $CH_2OH$, $CH_2NH_2$, CONR'R" wherein R' and R" can be the same or different; alone, or in a mixture; and, (b) from about 0 to about 4% by wt. of 3-methylcatechol, 3-methoxycatechol, or 3,6-dimeethylcatechol as a color modifier; and,
(2) about 1 to about 10% by wt. of an oxidant selected from sodium periodate, periodic acid, other water-soluble salts of periodate, and any of the isolated equilibrium species of periodate.

2. A dye composition, according to claim 1, wherein said hydroxyindole dye precursor is 4-hydroxyindole, 5-hydroxyindole, 6-hydroxyindole, 7-hydroxyindole, indole-5-hydroxy-3-acetic acid, indole-5-hydroxy-3-hydroxyethyl, indole-5-hydroxy-2-carboxylic acid or indole-5-hydroxy-2-hydroxymethyl; alone, or in a mixture, and the oxidant is sodium periodate.

3. A dye composition, according to claim 1, wherein said oxidant is sodium periodate.

4. A dye composition, according to claim 1, wherein a thickener is present at about 0.1 to about 25% by wt. to minimize dripping from the hair.

5. A dye composition, according to claim 1, wherein 3-methylcatechol, 3-methoxycatechol, or 3,6-dimethylcatechol is present as a color modifier in a concentration of from about 0.1 to about 4% by wt.

6. A dye composition, according to claim 1, wherein a stabilizer is present at a concentration of about 0.5 to about 5 mM.

7. A dye composition, according to claim 6, wherein said stabilizer is ascorbic acid.

8. A process for dyeing hair which comprises
(1) contacting hair with a composition consisting essentially of about 0.1 to about 10% by wt. of a hydroxyindole dye precursor of the formula

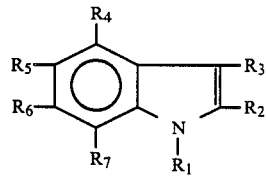

wherein
$R_1$ is H or alkyl (1-4C);
$R_4$, $R_5$, $R_6$, $R_7$ can be the same or different but one must be OH and the others selected from: H, alkyl (1-4C), $NH_2$, COOR' (R' is alkyl 1-4C or H), $CONH_2$, halogen (Cl, Br, I, F), OR" (R" is alkyl 1-4C); $CH_2OH$, $CH_2NH_2$, CONR'R" wherein R' and R" can be the same or different;
R, $R_3$ can be the same or different and are: H, OH, alkyl (1-4C), $NH_2$, COOR' (R' is alkyl 1-4C or H), $CONH_2$, halogen (Cl, Br, I, F), OR" (R" is alkyl 1-4C); $CH_2OH$, $CH_2NH_2$, CONR'R" wherein R' and R" can be the same or different; alone, or in a mixture; for about 3 min to about 30 min;
(2) rinsing the hair with water;
(3) patting the hair dry;
(4) contacting the rinsed and dried hair with a solution of about 5 to about 10% by wt. of sodium periodate, at about 20° to about 30° C. for about 5 to about 30 min; and
(5) rinsing the dyed hair with water.

9. A process according to claim 8, wherein said hydroxyindole dye precursor is 4-hydroxyindole, 5-hydroxyindole, 6-hydroxyindole, 7-hydroxyindole, indole-5-hydroxy-3-acetic acid, indole-5-hydroxy-3-hydroxyethyl, indole-5-hydroxy-2-carboxylic acid or indole-5-hydroxy-2-hydroxymethyl; alone, or in a mixture, and the oxidant is sodium periodate.

10. A process, according to claim 8, wherein a thickener at about 0.1 to about 25% by wt. to minimize dripping from the hair is added to the dye composition.

11. A process, according to claim 8, wherein about 0.1 to about 10% by wt. of 3-methylcatechol, 3-methoxycatechol, or 3,6-dimethylcatechol is added to the dye composition as a color modifier.

12. A process, according to claim 8, wherein a stabilizer is added to the dye composition at a concentration of 1 to about 5 mM.

13. A process, according to claim 12, wherein said stabilizer is ascorbic acid.

14. A process for dyeing hair which comprises
(1) contacting hair with a dye composition consisting essentially of:
(a) a hydroxyindole dye precursor of the following formula, present at a concentration of from about 0.1 to about 10% by wt.:

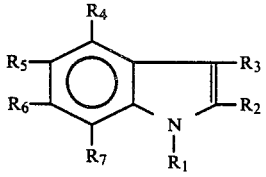

wherein
$R_1$ is H or alkyl (1-4C);

R4, R5, R6, R7 can be the same or different but one must be OH and the others selected from: H, alkyl (1-4C), NH2, COOR' (R' is alkyl 1-4C or H), CONH2, halogen (Cl, Br, I, F), OR" (R" is alkyl 1-4C); CH2OH, CH2NH2, CONR'R" wherein R' and R" can be the same or different; R2, R3 can be the same or different and are: H, OH, alkyl (1-4C), NH2, COOR' (R' is alkyl 1-4C or H), CONH2, halogen (Cl, Br, I, F), OR" (R" is alkyl 1-4C); CH2OH, CH2NH2, CONR'R" wherein R' and R" can be the same or different; alone, or in a mixture; and (b) a surfactant at a concentration of from about 0.1 to about 10% by wt.;

(2) waiting of about 3 to about 15 min;

(3) contacting and working into the hair a solution of about 5 to about 10% by wt. of sodium periodate, at about 20° to about 30° C. for about 5 to about 30 min; and (4) rinsing the dyed hair with water.

15. A process according to claim 14 wherein said hydroxyindole dye precursor is 4-hydroxyindole, 5-hydroxyindole, 6-hydroxyindole, 7-hydroxyindole indole-5-hydroxy-3-acetic acid, indole-5-hydroxy-3-hydroxyethyl, indole-5-hydroxy-2-carboxylic acid or indole-5-hydroxy-2-hydroxymethyl; alone, or in a mixture, and the oxidant is sodium periodate.

16. A process, according to claim 14, wherein about 0.1 to about 25% by wt. of a thickener selected from the group consisting of water-soluble resins and gums, polymers, and inorganic materials, to minimize dropping from the hair is added to the dye composition.

17. A process, according to claim 14, wherein about 0.1 to about 10% by wt. of 3-methylcatechol, 3-methoxycatechol, or 3,6-dimethylcatechol is added to the dye composition as a color modifier.

18. A process, according to claim 14, wherein a stabilizer is added to the dye composition at a concentration of 1 to about 5 mM.

19. A process, according to claim 18, wherein said stabilizer is ascorbic acid.

20. A process, according to claim 14, wherein said surfactant is disodium laureth sulfo succinate, TEA lauryl sulfate, laureth-4, laureth-23, sodium laurel sulfate, phosphate esters, or sodium lauryl ether sulfo succinate, alone or in a mixture.

21. A dye composition for dyeing skin comprising
(1) about 0.1 dye precursor consisting of from to about 10% by wt. of a hydroxyindole dye precursor of the formula

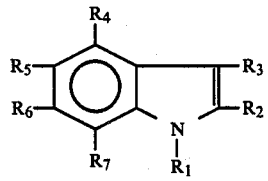

wherein
R1 is H or alkyl (1-4C);
R4, R5, R6, R7 can be the same or different but one must be OH and the others selected from: H, alkyl (1-4C), NH2, COOR' (R' is alkyl 1-4C or H), CONH2, halogen (Cl, Br, I, F), OR" is alkyl 1-4C); CH2OH, CH2NH2, CONR'R" wherein R' and R" can be the same or different; R2, R3 can be the same or different and are: H, alkyl (1-4C), NH2, OH, COOR' (R' is alkyl 1-4C or H) CONH2, halogen (Cl, Br, I, F), OR" (R" is alkyl 1-4C); CH2OH, CH2NH2, CONR'R" wherein R' and R" can be the same or different; alone, or in a mixture; and (2) about 5 to about 15% by wt. of sodium periodate, potassium permanganate, sodium hypochlorite, potassium ferricyanide, potassium dichromate, ammonium persulfate, silver oxide, Fenton's reagent, ferric chloride, lead (IV) oxide, cesium (IV) sulfate, or oxygen in the presence of UV light.

22. A dye composition, according to claim 21, wherein said hydroxyindole dye precursor is 4-hydroxyindole, 5-hydroxyindole, 6-hydroxyindole, 7-hydroxyindole, indole-5-hydroxy-3-acetic acid, indole-5-hydroxy-3-hydroxyethyl, indole-5-hydroxy-2-carboxylic acid or indole-5-hydroxy-2-hydroxymethyl; alone or in a mixture, and the oxidant is sodium periodate.

23. A dye composition, according to claim 21, wherein said hydroxyindole dye precursor is present at a concentration of about 0.1 to about 10% by wt. and the concentration of sodium periodate is from about 1 to about 10% by wt.

24. A process for dyeing skin consisting essentially of
(1) contacting skin with a dye composition wherein the dye precursors consists of from about 0.1 to about 10% by wt. of a dye precursor of the formula

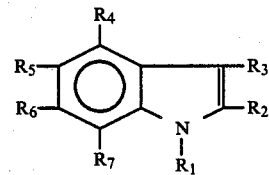

wherein
R1 i H or alkyl (1-4C);
R4, R5, R6, R7 can be the same or different but one must be OH and the others selected from: H, alkyl (1-4C), NH2, COOR' (R' is alkyl 1-4C or H), CONH2, halogen (Cl, Br, I, F), OR" (R" is alkyl 1-4C); CH2OH, CH2NH2, CONR'R" wherein R' and R" can be the same or different; R2, R3 can be the same or different and are: H, OH, alkyl (1-4C), NH2, COOR' (R' is alkyl 1-4C or H) CONH2, halogen (Cl, Br, I, F), OR" (R" is alkyl 1-4C); CH2OH, CH2NH2, CONR'R" wherein R' and R" can be the same or different; alone, or in a mixture;

(2) contacting the skin with an equal volume of about 10% by wt. of an oxidant selected from sodium periodate, potassium permanganate, sodium hypochlorite, potassium ferricyanide, potassium dichromate, ammonium persulfate, silver oxide, Fenton's reagent, ferric chloride, lead (IV) oxide, or cesium (IV) sulfate; or exposing the skin to UV light; and permitting the treatment to continue for about 15 min; and (3) rinsing the dye away from the skin with water.

25. A process for dyeing skin consisting essentially of
(1) preforming a hydroxyindole dye by treating a 2% by wt. solution of a hydroxyindole dye precursor wherein said dye precursor consists of a compound of the formula

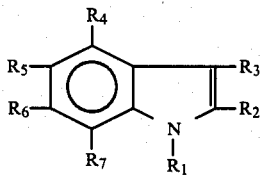

wherein $R_1$ is H or alkyl (1–4C);

$R_4$, $R_5$, $R_6$, $R_7$ can be the same or different but one must be OH and the others selected from: H, alkyl (1–4C), $NH_2$, COOR' (R') is alkyl 1–4C or H), $CONH_2$, halogen (Cl, Br, I, F), OR" is alkyl 1–4C); $CH_2OH$, $CH_2NH_2$, CONR'R" wherein R' and R" can be the same or different; $R_2$, $R_3$ can be the same or different and are: H, OH, alkyl (1–4C), $NH_2$, COOR' (R' is alkyl 1–4C or H) $CONH_2$, halogen (Cl, Br, I, F), OR" (R" is alkyl 1–4C); $CH_2OH$, $CH_2NH_2$, CONR'R" wherein R' and R" can be the same or different; alone, or in a mixture; with an equal volume of a 10% solution of an oxidant selected from sodium periodate, potassium permanganate, sodium hypochlorite, potassium ferricyanide, potassium dichromate, ammonium persulfate, silver oxide, Fenton's reagent, ferric chloride, lead (IV) oxide, or cesium (IV) sulfate; and collecting the precipitate formed after reacting for 15 min at room temperature;

(2) contacting the skin with a 2% by wt. preparation of the preformed dye in a volatile carrier;

(3) allowing the carrier to evaporate; and (4) rinsing the dye carrier away from the skin with water.

26. A process, according to claim 25, wherein said hydroxyindole dye precursor is 4-hydroxyindole, 5-hydroxyindole, 6-hydroxyindole, 7-hydroxyindole, indole-5-hydroxy-3-acetic acid, indole-5-hydroxy-3-hydroxyethyl, indole-5-hydroxy-2-carboxylic acid or indole-5-hydroxy-2-hydroxymethyl; alone, or in a mixture, and the oxidant is sodium periodate.

27. A process, according to claim 25, wherein the volatile carrier is ethanol.

* * * * *

UNITED STATES PATENT AND TRADEMARK OFFICE
CERTIFICATE OF CORRECTION

PATENT NO. : 4,776,857
DATED : October 11, 1988
INVENTOR(S) : James Carroll, Cynthia D. Millis, Walter C. Herlihy Page 1 of 2

It is certified that error appears in the above—identified patent and that said Letters Patent is hereby corrected as shown below:

| | |
|---|---|
| Column 2: | line 19: "malenin-like" should read --melanin-like--. |
| Column 3: | line 15: "onestep" should read --one-step--. |
| Column 5: | line 26: "is converting" should read --in converting--. |
| Column 6: | line 31: "metabilsulfite" should read --metabisulfite--; line 41: "ad" should read --and--; line 62: "hairlights" should read --highlights--. |
| Column 7: | line 40: "4hydroxyindole" should read --4-hydroxyindole--. |
| Column 9: | line 1: "may or may be" should read --may or may not be--. |
| Column 10: | line 42: "$H_4IO_6^- \longrightarrow H_3IO_6^{2-} + H^+$" should read --$H_4IO_6^- \rightleftharpoons H_3IO_6^{2-} + H^+$--; line 45: "$H_2I_2I_{10}^{4-}$" should read --$H_2I_2O_{10}^{4-}$--. |

UNITED STATES PATENT AND TRADEMARK OFFICE
CERTIFICATE OF CORRECTION

PATENT NO. : 4,776,857

DATED : October 11, 1988

INVENTOR(S) : James Carroll, Cynthia D. Millis, Walter C. Herlihy

It is certified that error appears in the above-identified patent and that said Letters Patent is hereby corrected as shown below:

Column 11: line 37: "dimeethylcatechol" should read --dimethylcatechol--.C

Column 12: line 18: "R, $R_3$" should read --$R_2$, $R_3$--.

Column 13: line 15: "waiting of" should read --waiting for--;
line 31: "dropping" should read --dripping--; lines 48-49: "about 0.1 dye precursor consisting of from about 10% by wt. of a" should read --a dye precursor consisting of from about 0.1 to about 10% by wt. of a--;
line 65: "OR'' is alkyl" should read --OR'' (R'' is alkyl--.

Column 14: line 40: "$R_1$ i H or alkyl" should read --$R_1$ is H or alkyl--.

Column 15: line 14: "(R')" should read --(R'--.

Signed and Sealed this

First Day of August, 1989

Attest:

DONALD J. QUIGG

Attesting Officer

Commissioner of Patents and Trademarks